(12) United States Patent
Wu et al.

(10) Patent No.: US 7,670,616 B2
(45) Date of Patent: Mar. 2, 2010

(54) HYDROGEL FORMING SYSTEM COMPRISING PEG DERIVATIVE PRECURSOR

(75) Inventors: Daqing Wu, Ithaca, NY (US); Chih-Chang Chu, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 1414 days.

(21) Appl. No.: 11/060,279

(22) Filed: Feb. 18, 2005

(65) Prior Publication Data

US 2005/0202060 A1 Sep. 15, 2005

Related U.S. Application Data

(60) Provisional application No. 60/551,793, filed on Mar. 11, 2004.

(51) Int. Cl.
*A61F 2/02* (2006.01)

(52) U.S. Cl. .................................................... 424/426
(58) Field of Classification Search ..................... None
See application file for complete search history.

(56) References Cited

U.S. PATENT DOCUMENTS 6,592,895 B2    7/2003    Lang et al. .................. 424/457

OTHER PUBLICATIONS

Wu, D., et al., "Synthesis, characterization and drug release from three-arm . . . diacrylate hydrogels", J. Biomater. Sci. Polymer Edn., vol. 14, No. 8, pp. 777-802 (2003).
Lang, M., et al., "Synthesis and Structural Analysis of Functionalized Poly (ε-caprolactone)-Based Three-Arm Star Ploymers", J. Poly. Sc., Part A: Polymer Chem., vol. 40, 1127-1141 (2002).

*Primary Examiner*—Carlos A Azpuru
(74) *Attorney, Agent, or Firm*—Bacon & Thomas, PLLC

(57) ABSTRACT

Variation in precursor ratio and mass of double bond functionalized polyhydric alcohol precursor and polyethylene glycol diacrylate precursor provide a wide range of release rates of drug or other biologically active agent from hydrogel formed therefrom.

13 Claims, No Drawings

HYDROGEL FORMING SYSTEM COMPRISING PEG DERIVATIVE PRECURSOR

This application claims the benefit of U.S. Provisional Application No. 60/551,793, filed on Mar. 11, 2004, the whole of which is incorporated herein by reference.

TECHNICAL FIELD

This invention is directed at a biodegradable hydrogel forming system with hydrophobic and hydrophilic components.

BACKGROUND OF THE INVENTION

U.S. Pat. No. 6,592,895 is directed at precursor polyhydric alcohol esters where acyl moieties originate from aliphatic homopolymer or copolymer polyesters which contain free hydroxyl at their terminal ends where some or each of the free hydroxyls are reacted to provide 2-carboxy-ethenyl groups. These are indicated as being useful for the formation of hydrogels for delivery of drugs or other biologically active agents, for example, from hydrogel coating on vascular stents.

SUMMARY OF THE INVENTION

It has been discovered herein that the range of swelling properties and drug delivery profiles of hydrogels from precursor polyhydric alcohol ester of U.S. Pat. No. 6,592,895 can be expanded by using said polyhydric alcohol esters precursor in combination with polyethylene glycol diacrylate precursor.

One embodiment of the invention herein is directed to a biodegradable hydrogel forming system comprising a hydrophobic component containing at least one unsaturated group terminal moiety and a hydrophilic component which is poly(ethylene glycol) diacrylate, where the hydrophobic component and hydrophilic component constitute different compounds from one another. The hydrophobic component is preferably polyhydric alcohol ester with acyl moieties where some or each of the acyl moieties contain a terminal 2-carboxy ethenyl group as described in U.S. Pat. No. 6,592,895, e.g., polyhydric alcohol ester where the alcohol moiety originates from a polyhydric alcohol containing from 3 to 6 hydroxyl groups, e.g., glycerol, and the acyl moieties originate from poly(epsilon-caprolactone) where some or each acyl moiety is functionalized to contain 2-carboxy ethenyl group.

In other embodiments of the invention herein, there is provided delivery system comprising hydrogel formed from the hydrogel forming system of the first embodiment, for delivery and/or release of drug or other biologically active agent from said hydrogel, and vascular stent containing coating comprising said delivery system.

DETAILED DESCRIPTION

We turn now to the embodiment of the invention herein, which is directed to a biodegradable hydrogel forming system comprising a hydrophobic component containing at least one unsaturated group terminal moiety and a hydrophilic component which is poly(ethylene glycol) diacrylate, where the hydrophobic component and the hydrophilic component constitute different compounds from one another.

We turn firstly to the hydrophobic component, which preferably is polyhydric alcohol ester as described in U.S. Pat. No. 6,592,895 where some or each of the acyl moieties contain terminal 2-carboxy ethenyl group and acyl moieties originate from aliphatic homopolymer or copolymer polyesters and contain free hydroxyl at their terminal ends and have weight average molecular weight ranging from 1,000 to 80,000, where some or each of the free hydroxyls are functionalized to incorporate unsaturated group, e.g., reacted to provide unsaturated terminal moiety which is 2-carboxy ethenyl group, and alcohol moieties originate from polyhydric alcohol containing from 3 to 6 hydroxyl groups. The hydrophobic component used in working example herein, denoted PGCL-Ma, has alcohol moiety originating from glycerol and acyl moiety originating from poly(epsilon-caprolactone) where some or each of the terminal end free hydroxyls of the poly(epsilon-caprolactone) are reacted with maleic anhydride to provide unsaturated terminal moieties which are 2-carboxy ethenyl groups. These polyhydric alcohol esters can be prepared as described in U.S. Pat. No. 6,592,895 and Lang, M., et al, Journal of Polymer Science: Part A: Polymer Chemistry Vol 40, 1127-1141 (2002). The weight average molecular weights herein are determined by gel permeation chromatography, vs. monodispersed polystyrene standards.

We turn now to the poly(ethylene glycol) diacrylate hydrophilic component. It has the formula:

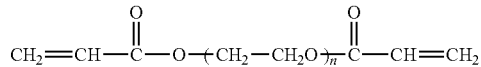

where n ranges from 8 to 400 e.g., from 40 to 180.

The polyethylene glycols (PEGs) used to produce the poly(ethylene glycol) diacrylate (PEGDA) for the working examples herein, were PEG diol with mass of 2, 3.6 and 8 kDa. The poly(ethylene glycol) diacrylate can be synthesized according to the procedure of Cruise, G. M., et al, Biomaterials, 19, 1287 (1998) and was synthesized in this way for the PEGDA of the working example.

In the hydrogel forming systems herein, the weight ratio of hydrophobic component to hydrophilic component can range, for example, from 1:99 to 99:1, e.g., from 20:80 to 80:20.

Hydrogels are readily formed from the hydrogel forming systems herein by dissolving the hydrophobic and hydrophilic precursors in a common solvent, preferably dimethylformamide, together with photoinitiator, e.g., 2,2-dimethoxy 2-phenyl acetophenone (DMPA), e.g., present at 0.1 to 5%, e.g., 1 to 5% by weight of the precursors, with both precursors together being present preferably at a total concentration of 20 to 40% in solution in the common solvent and then exposing the solution to low-intensity UV irradiation (e.g. 365 nm, 8 W) for 2 to 6 hours to cause photocrosslinking between the molecules of the same and the different precursors.

The hydrogels herein are advantageous compared to those of U.S. Pat. No. 6,592,895 in having a wider range of swelling properties and drug release profiles as shown in the working example. When swelling ratio is increased, drug release is hastened (more is released faster). The swelling ratio has been found to increase with increase in ratio of hydrophilic to hydrophobic components and with increase in molecular weight of each of the components. Moreover, the presence of poly(ethylene glycol) in one precursor is a positive as it is recognized as a very preferred drug carrier by the pharmaceutical industry.

We turn now to delivery and/or release of drug or other biologically active agent from hydrogel carrying such.

The same method for entrapping drug or other biologically active agent can be used as is described in connection with indomethacin as drug in a different hydrogel in WO 00/60956 published Oct. 19, 2003. In the example herein and in the invention as illustrated in Wu, D., et al, J. Biomater. Sci. Polym Edn. 14(8), 777-802(2003), drug was added to the precursor solution prior to photocrosslinking to entrap the drug. Typically, the hydrogel contains, for example, a drug loading ranging from 0.5 to 5 wt percent (w/w) based on the total weight of the polymer precursors.

Alternatively, drug or other biologically active agent can be covalently bonded to one or both of the precursors.

In the working example herein, bovine serum albumin (BSA) was used to represent drug or other biologically active agent to evaluate swelling ratio and drug release profile.

We turn now to case where hydrogel forming system herein is used to form a delivery system comprising hydrogel entrapping or covalently bonded to drug or other biologically active agent to be delivered and/or released, coated on a vascular stent, e.g., a cardiac stent. The drugs/biologically active agents for the coatings can be those set forth in column 7 of U.S. Pat. No. 6,592,895 and formation of hydrogel drug/other biologically active agent coating delivery/release system on a stent can be carried out as described in column 7 of U.S. Pat. No. 6,592,895.

The invention is supported by disclosure and data in Wu, D., et al, J. Biomaterial Sci. Polymer Edn, Vol. 14, No. 8, 777-802 (2003) which published in August 2003 (hereinafter Wu et al) and which is incorporated herein by reference.

The invention is illustrated by the following working example.

Polyhydric alcohol ester was prepared by ring opening polymerization of epsilon-caprolactone in the presence of glycerol and reaction of maleic anhydride with some or each of free hydroxyls at terminal end of acyl moiety of intermediate polyhydric alcohol ester. The ring opening polymerization of epsilon-caprolactone in the presence of glycerol was carried out to produce intermediates denoted PGCL-OH-1, PGCL-OH-2 and PGCL-OH-3 as described in Lang, M., et al Journal of Polymer Science, Part A: Polymer Chemistry, Vol 40, 1127-1141 (2002). The PGCL-OH-1, PGCL-OH-2 and PGCL-OH-3 each had different molecular weights as set forth in Tables 1 and 2 of Lang, M., et al, Journal of Polymer Science: Part A: Polymer Chemestry, Vol 40, 1127-1141 (2002) and were respectively converted to PGCL-Ma precursors of 2.4, 5.6 and 13 kDa as follows: PGCL-OH-1, PGCL-OH-2 and PGCL-OH-3 were each placed in a different three-necked flask along with 5 equivalents of maleic anhydride under $N_2$ environment and heated to 130 C for 1 day. In each case, processing was then carried out as follows: The reaction mixture was cooled to room temperature and dissolved in chloroform. The chloroform solution was poured into excess petroleum ether to precipitate the product which was denoted PGCL-Ma. The powder precipitate was stirred in 500 ml distilled water for 4 hours for removing any excess maleic anhydride. After filtration, the precipitate was washed with distilled water four times and dried over $P_2O_5$ in vacuum at room temperature until a constant weight was obtained. As indicated above, PGCL-Ma precursors of 2.4, 5.6, and 13 kDa were obtained.

We turn now to the preparation of the poly(ethylene glycol) diacrylate precursor denoted PEGDA. Synthesis was carried out as described in Cruise, G. M., et al, Biomaterials 19, 1287 (1998). Poly(ethylene glycol) diol starting material of 2, 3.6 and 8 kDa was purchased from Sigma.

To prepare hybrid networks, the PGCL-Ma and PEGDA at composition ratios as described below were dissolved in dimethylformamide to make 40% (w/v) concentration solutions. The PGCL-Ma to PEGDA weight ratios were 100% PGCL-Ma (100:0), 70:30, 50:50, 30:70 and 100% PEGDA (0:100).

A photo-initiator, 2,2-dimethoxy 2-phenyl acetophenone (DMPA), 0.1% (w/w) of the precursors, was added to the precursor solution. Resulting solution was homogenous and 2 ml of it was irradiated by a long-wavelength UV lamp (365 nm, 8 W) at room temperature for 3 hours. The solvent remaining in the photocrosslinked networks was evaporated under vacuum at room temperature and dried to constant weight.

Swelling testing was carried out as described in Wu et al. A graph of swelling ratios of PGCL-Ma (5600)/PEGDA (3600) (PGCL-Ma of 5.6 kDa and PEGDA of 3.6 kDa) hydrogels at different composition ratios is depicted in FIG. 6 of Wu et al. The data shows an initial burst swelling characteristic of hydrophilic polymer networks upon immersion in water followed by a gradual swelling phase. The extent of initial increase increased with increase in PEGDA content and the increase in overall swelling ratio increased with increase in PEGDA content.

Testing was also carried out to determine effect on swelling ratio of different molecular masses of PGCL-Ma and PEGDA components. Swelling ratio (%) determined in phosphate buffered saline (PBS), pH 7.4, at 37 C, is set forth in FIG. 7 of Wu et al. As indicated in said FIG. 7, increases in molecular mass of each component was found to increase swelling ratio.

Bovine serum albumin (BSA) was selected to provide agent for determination of drug release profile. Testing was carried out as set forth in the paragraph denoted "In vitro BSA release from PGCL-Ma/PEGDA hydrogels" at pages 797-800 of Wu et al.

Results are shown in FIGS. 12 and 13 of Wu et al. For said FIGS. 12 and 13, the 5.6 kDa molecular weight PGCL-Ma and 3.6 kDa PEGDA were used. As shown in FIG. 12, the PGCL-Ma/PEGDA hybrid networks having a high relative PGCL-Ma component presence showed slower release rates and lower amounts of BSA were released than in those hybrid networks having higher relative amount of PEGDA components. As shown in FIG. 13, the cumulative percentage of released BSA with 1% initial loading concentration was higher than with 2.5% initial loading, in the same hydrogel.

The data shows that by changing the composition ratio of PGCL-Ma to PEGDA, a wide range of in vitro release profiles were obtained.

VARIATIONS

Variations will be obvious to those skilled in the art. Therefore, the scope of the invention is determined by the scope of the claims.

What is claimed is:

1. A biodegradable hydrogel forming system comprising a hydrophobic component containing at least one unsaturated group terminal moiety and a hydrophilic component which is poly(ethylene glycol) diacrylate where the hydrophobic component and hydrophilic component constitute different compounds from one another.

2. The biodegradable hydrogel forming system of claim 1 where the weight ratio of said hydrophobic component to the weight ratio of said hydrophilic component ranges from 1:99 to 99:1, for example from 80:20 to 20:80.

3. The biodegradable hydrogel forming system of claim 2 where said hydrophobic component is a biodegradable polyhydric alcohol ester where the acyl moieties of the ester originate from aliphatic homopolymer or copolymer polyester which contains free hydroxyl at its terminal end where some or each of the acyl moieties are functionalized to incorporate an unsaturated terminal moiety and where the weight average molecular weight of the ester ranges from 1,000 to 80,000.

4. The biodegradable hydrogel forming system of claim 3 where alcohol moiety of the polyhydric alcohol ester originates from a polyhydric alcohol containing from 3 to 6 hydroxyl groups.

5. The biodegradable hydrogel forming system of claim 4 where unsaturated group terminal moiety is a 2-carboxy ethenyl group.

6. The biodegradable hydrogel forming system of claim 4 where each acyl moiety of the said polyhydric alcohol ester is poly(epsilon-caprolactone) where some or each free hydroxyl is functionalized to provide unsaturated group terminal moiety which is a 2-carboxy ethenyl group.

7. The biodegradable hydrogel forming system of claim 6 where the alcohol moiety of the polyhydric alcohol ester originates from glycerol.

8. The biodegradable hydrogel forming system of claim 7 where the poly(ethylene glycol) diacrylate has the formula:

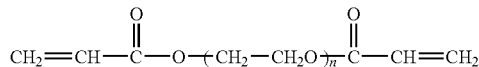

where n ranges from 8 to 400.

9. The biodegradable hydrogel forming system of claim 2 where the poly(ethylene glycol) diacrylate has the formula:

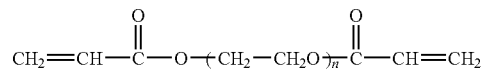

where n ranges from 8 to 400.

10. Biodegradable hydrogel formed from the hydrogel forming system of claim 9.

11. Biodegradable hydrogel formed from the hydrogel forming system of claim 8.

12. Delivery system comprising the biodegradable hydrogel of claim 10 entrapping or covalently bonded to drug or other biologically active agent to be delivered and/or released.

13. Delivery and/or release system comprising the biodegradable hydrogel of claim 11 entrapping or covalently bonded to drug or other biologically active agent to be delivered and/or released.

* * * * *

UNITED STATES PATENT AND TRADEMARK OFFICE
CERTIFICATE OF CORRECTION

| | |
|---|---|
| PATENT NO. | : 7,670,616 B2 |
| APPLICATION NO. | : 11/060279 |
| DATED | : March 2, 2010 |
| INVENTOR(S) | : Daqing Wu et al. |

It is certified that error appears in the above-identified patent and that said Letters Patent is hereby corrected as shown below:

Claim 2 (column 4, line 61), change ", for example" to -- or --.

Signed and Sealed this

Sixth Day of April, 2010

David J. Kappos
*Director of the United States Patent and Trademark Office*